United States Patent [19]

Saito et al.

[11] Patent Number: 5,334,348
[45] Date of Patent: Aug. 2, 1994

[54] URINE SAMPLER

[75] Inventors: Koichiro Saito, Tokyo; Kaoru Shimizu, Kisai, both of Japan

[73] Assignee: Yoshisuke Sakai, Fukuoka, Japan

[21] Appl. No.: 972,514

[22] Filed: Nov. 6, 1992

[30] Foreign Application Priority Data

Nov. 8, 1991 [JP] Japan .................................. 3-319727

[51] Int. Cl.$^5$ ............................................. G01N 33/50
[52] U.S. Cl. .................................. 422/61; D7/300.2;
128/761; 128/763; 128/767; 239/33; 422/100;
422/102
[58] Field of Search ............................ 422/61, 99–102,
422/312; 128/761, 763, 767; 239/33; D7/300.2

[56] References Cited

U.S. PATENT DOCUMENTS

| | | | |
|---|---|---|---|
| 2,943,794 | 7/1960 | Sussman | 239/33 |
| 4,494,581 | 1/1985 | Gordon | 422/102 |
| 5,055,258 | 10/1991 | Brodt et al. | 422/61 |

Primary Examiner—Jill A. Johnston
Attorney, Agent, or Firm—Davis Hoxie Faithfull & Hapgood

[57] ABSTRACT

In one configuration, a urine sampler comprises a hollow, cylindrical main stick body that is closed at least at one end and has a plurality of urine collection apertures formed in the wall thereof and, in another, comprises a urine collector having a long rod-shaped handle, a urine collection member constituted continuously with the handle and provided with urine collection apertures and a urine accumulator constituted continuously with the base of the urine collection member, and a urine storage capsule having a cutter for cutting a portion of the urine collector, a urine container for receiving urine flowing in from the urine collector and a lid. In the second configuration, the urine collector and the urine storage capsule are separate units. The urine sampler of either configuration is compact and extremely easy to use for collecting a urine sample of the minimum required quantity and, moreover, enables the collected sample to be safely transferred without spilling.

10 Claims, 6 Drawing Sheets

FIG.1
FIG.2
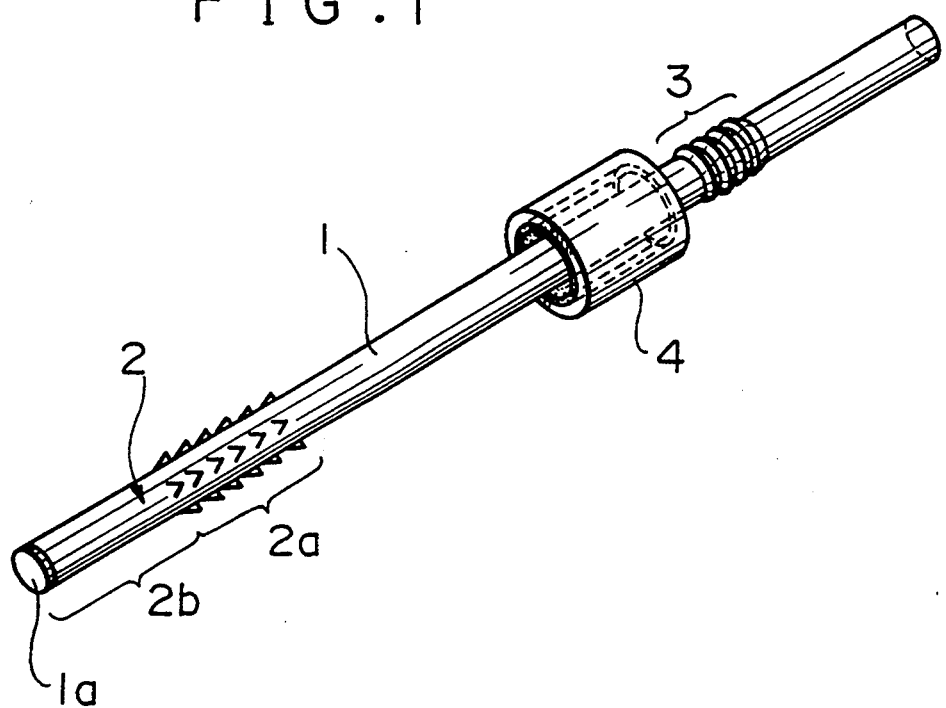
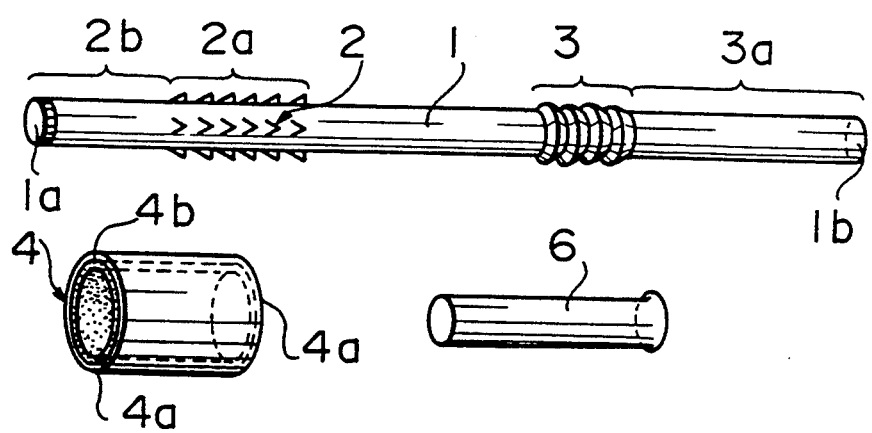

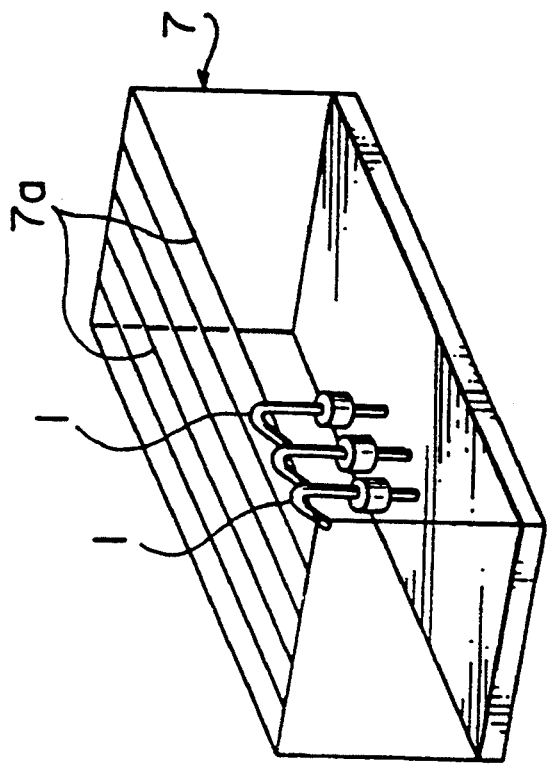
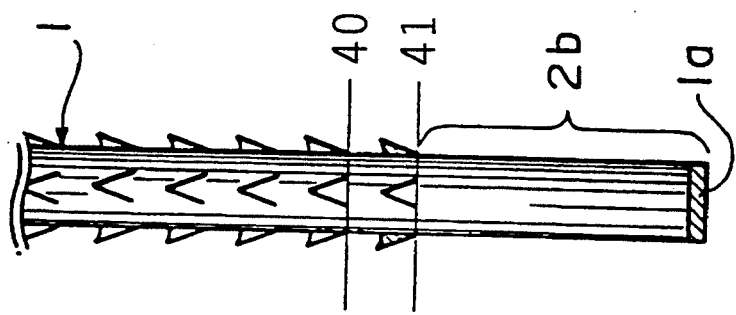

FIG. 5
FIG. 6
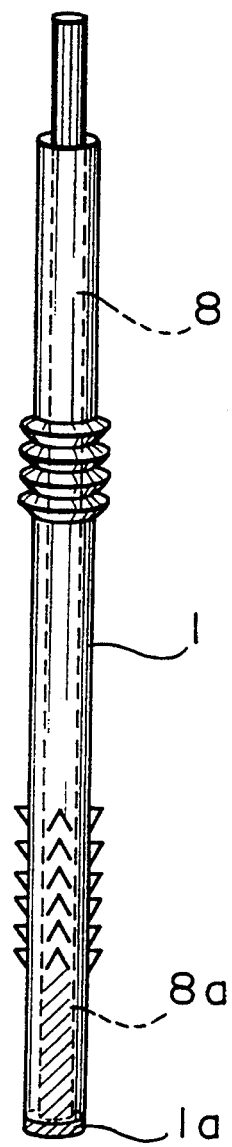
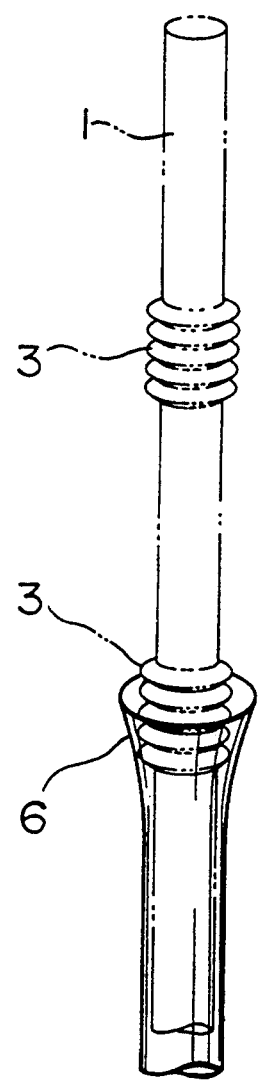

URINE SAMPLER

BACKGROUND OF THE INVENTION

1. Field of the Invention

This invention relates to a urine sampler for use in conducting urinalysis at schools, hospitals, test centers and the like.

2. Description of the Prior Art

Urinalysis, a test that can provide important information for early detection of diseases of the internal organs and otherwise determining the state of the subject's health, can be conducted with no discomfort to the subject and with minimal trouble to those conducting the test. This has led hospitals and test centers to routinely test the urine of large numbers of new patients, persons having medical checkups, hospitalized patients and others.

Ordinarily, the subject goes to a toilet to collect a urine sample in a paper cup and then either places the cup on a designated shelf in a lavatory or dips a test paper into the urine and places only the wetted test paper at a designated place. After a prescribed number of the paper cups containing the samples have been collected from the designated lavatories etc. and brought to the laboratory, the samples are analyzed.

This conventional method of analyzing urine samples collected in paper cups has a number of drawbacks. One is that some people have difficulty getting the urine into the paper cup. This is particularly true of female and elderly persons, who frequently also get urine on their hands and clothing. The method thus has a sanitation problem. In addition, much care is required in handling the collected samples because there is a danger of tipping over the cup when immersing a test paper in the urine or of spilling urine from the cup when carrying it to the designated place.

When, as is frequently the case, a large number of urine samples are tested throughout the day, the wide-mouthed cups, which have to be placed side by side, take up considerable space so that a fairly large area has to be reserved for storing them until the time of testing. There is also a danger of losing all or part of the contents of some of the cups by dropping or tilting them at the time of moving them to the laboratory. This not only fouls the surroundings but may make it impossible to test some samples. Another problem is that many subjects collect larger samples than necessary. As a result, when the samples of a large number of subjects are brought together, they produce a pungent odor which may distract and lower the working efficiency of the doctors, nurses and other personnel who conduct the urinalysis.

SUMMARY OF THE INVENTION

The object of this invention is to provide a compact urine sampler which is extremely easy to use for collecting a urine sample of the minimum required quantity and which enables the collected sample to be safely transferred, without spilling, to a sealed container.

For achieving this object, one aspect of the invention provides a urine sampler having a stick-shaped main body constituting a urine collection device. The stick-shaped main body is a cylindrical stick closed at least at one end and having a plurality of urine collection apertures formed in the wall thereof.

Another aspect of the invention provides a urine sampler comprising a urine collector and a urine storage capsule, wherein the urine collector has a long rod-shaped handle, a conical urine collection member constituted continuously with the handle and provided with urine collection apertures and a urine accumulator constituted continuously with the base of the urine collection member, and the urine storage capsule has a cutter for cutting a portion of the urine collector, a urine container for receiving urine flowing in from the urine collector and a lid.

With the urine sampler according to either of these aspects of the invention, when urine is passed onto the urine collection apertures of the stick-shaped main body or the urine collection apertures of the urine collector, the minimum required amount of urine passes through the urine collection apertures to be stored inside the stick-shaped main body or in the urine accumulator. By holding the urine sampler by the long rod-shaped handle and urinating onto the urine collection apertures, the user can easily cause a urine sample of the minimum required volume to be collected through the urine collection apertures into the urine accumulator. Moreover, in the arrangement in which the urine collector and the urine storage capsule are separately constituted, after urine has been collected in the urine accumulator, the accumulated urine can be transferred to the urine container by forcing the cutter of the urine container onto the bottom of the urine accumulator so as to pierce the bottom of the urine collector and allow the urine to flow from the urine accumulator into the urine container. Then once the urine container has been tightly closed with the lid, the urine storage capsule can be carried or transported standing upright with the collected urine stored therein.

BRIEF DESCRIPTION OF THE DRAWINGS

FIG. 1 is a perspective view of a urine sampling stick.

FIG. 2 is a perspective view of the individual components of the urine sampling stick of FIG. 1.

FIG. 3 is a partial view of the urine sampling stick of FIG. 1, for showing the amount of urine collected.

FIG. 4 is perspective view of a urine sampling stick holder.

FIG. 5 is partial view of the urine sampling stick of FIG. 1, for showing how a test paper is inserted.

FIG. 6 is perspective view showing another embodiment of the urine sampling stick.

DETAILED DESCRIPTION OF THE PREFERRED EMBODIMENTS

The invention will now be explained with reference to the drawings.

A stick type urine sampler that is an embodiment of this invention is shown in the perspective view of FIG. 1. The components of the urine sampling stick are shown in FIG. 2. While the stick can be constituted in various sizes, for the purposes of the present embodiment it will be assumed to be 6 mm in diameter and 210 mm in length. The urine sampling stick of this embodiment comprises a main stick body 1, a cover cylinder 4 and a cap 6.

Figure 7:
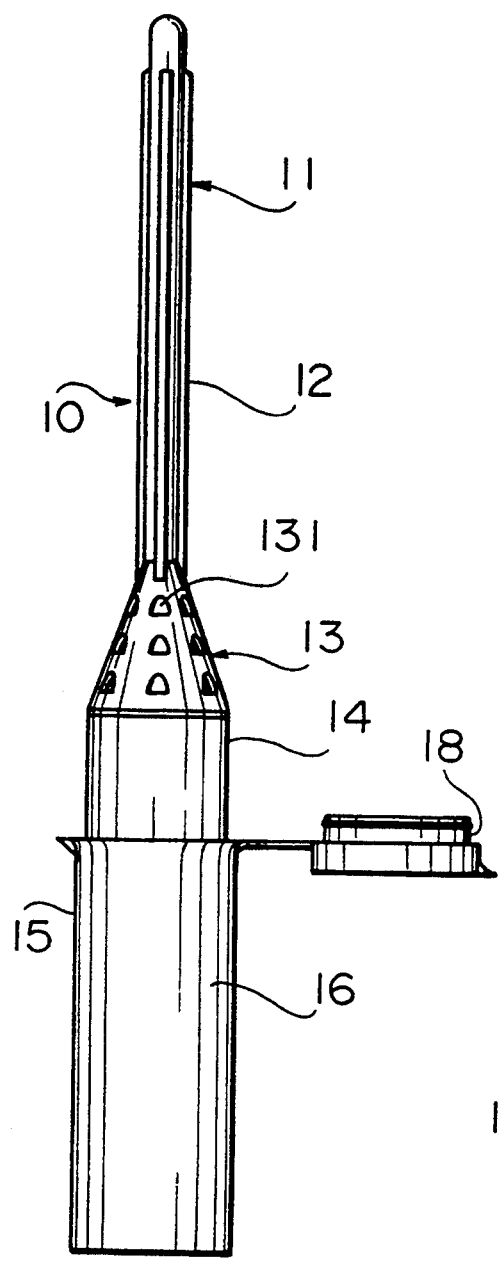
FIG. 7 is a front view of an embodiment of a urine collection device.
Figure 8:
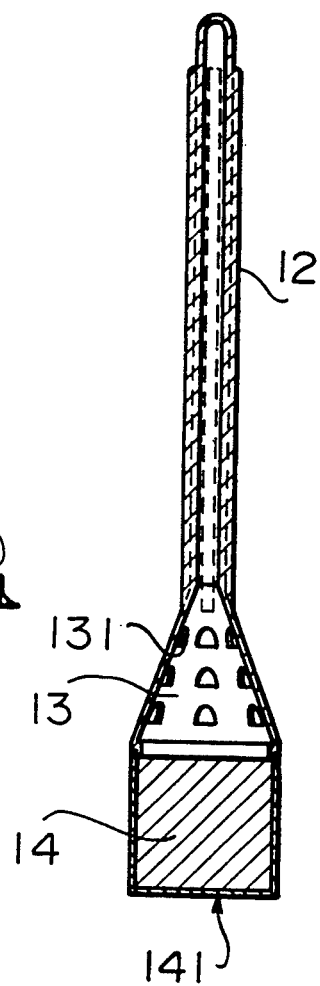
FIG. 8 a sectional view of the urine collector of the urine collection device of FIG. 7.
Figure 9:
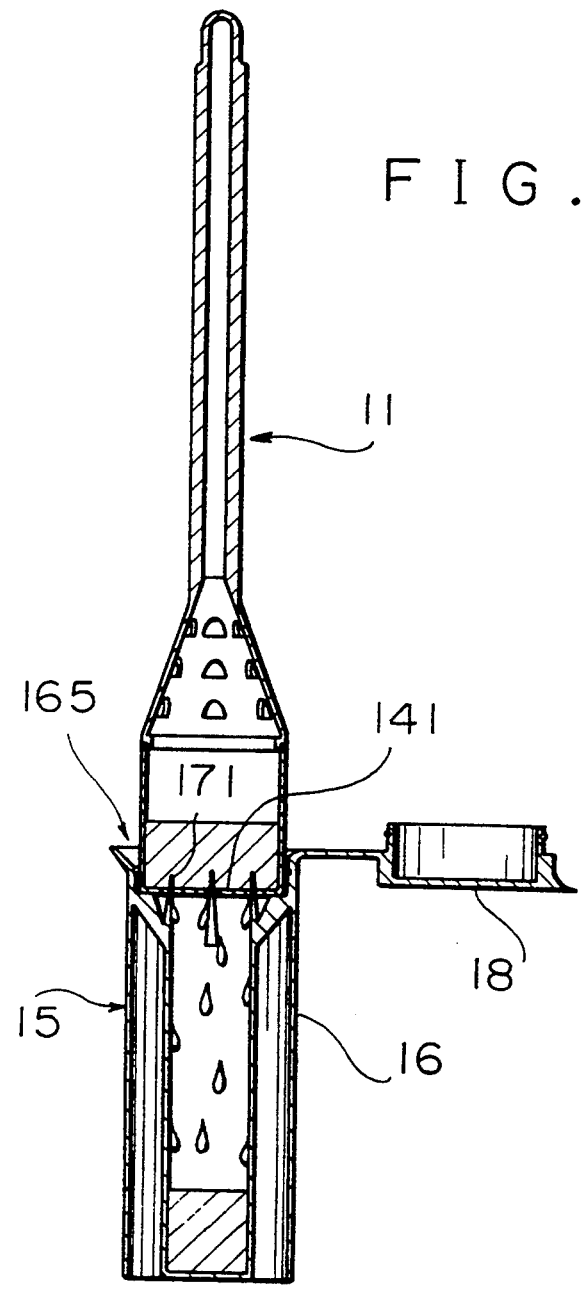
FIG. 9 is sectional view of the urine collection device of FIG. 7 showing a urine capsule thereof joined with the urine collector.
Figure 10:
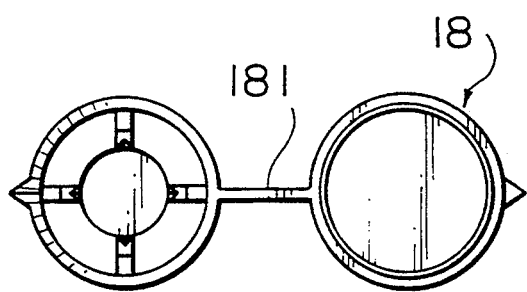
FIG. 10 a plan view showing a cutter and the underside of a lid of the urine storage capsule.
Figure 11:
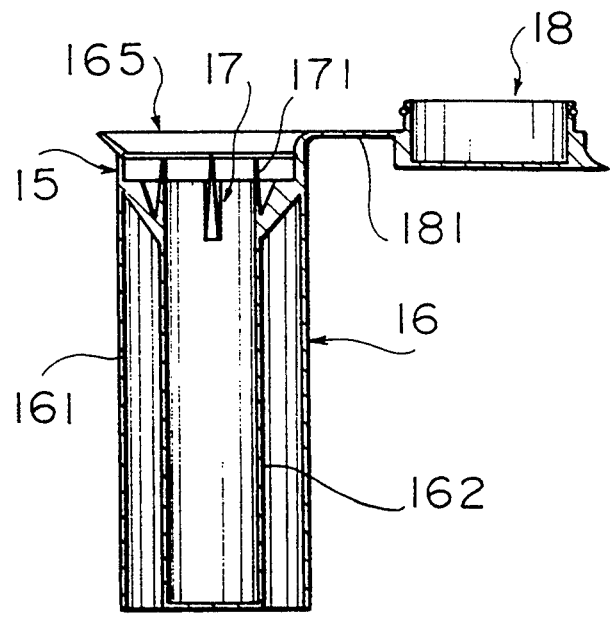
FIG. 11 is a sectional view of the urine storage capsule.

A front view of a urine collection device 10 that is another embodiment of the invention is shown in FIG. 7, a sectional view of a urine collector 11 of this embodiment is shown in FIG. 8, a sectional view of the urine collection device 10 joined with a urine storage capsule 15 is shown in FIG. 9, a plan view of a cutter 17 of the urine storage capsule 15 and the underside of a lid thereof is shown in FIG. 10, and a sectional view of the urine storage capsule 15 is shown in FIG. 11.

The main stick body 1 of the stick type urine sampler is a colorless transparent or semitransparent straw. The whole urine sampler should be constituted of materials that do not produce noxious gases when burned. One end of the main stick body 1 is closed by a plug 1a and the other end is left open. The closed end will be referred to as the bottom end and the open end as the top end. The wall of the main stick body 1 near the bottom end is formed with a plurality of diagonal cuts 2 to serve as urine collection apertures. The part of the main stick body 1 provided with the cuts 2 constitutes a urine collection section 2a and the part thereof between the urine collection section 2a and the bottom end constitutes a urine storage section 2b. The tips of the cuts 2 project out from the outer surface of the wall of the main stick body 1. The main stick body 1 has a bellows-like corrugated section 3 near its top end.

The cover cylinder 4 has a prescribed length and is fitted on the main stick body 1 to be slidable between the urine collection section 2a and the corrugated section 3. The cover cylinder 4 consists of an outer cylinder portion 4a made of synthetic resin or metal and an inner cylinder portion 4b made of highly water absorbent waste paper or the like.

The cap 6 has an inner diameter enabling it to fit onto the main stick body 1 in snug contact with its outer wall surface and a length that is somewhat greater than the combined length of the urine storage section 2b and the urine collection section 2a. As shown in FIG. 2, the open end of the cap 6 is slightly flared to make it easy to fit onto the main stick body 1. To prevent confusion and enable easy identification of the collected urine samples in cases where many samples are tested at the same time, it is preferable to provide the cap 6 (and also the lid 18 explained below in connection with another embodiment) with a place for writing or attaching the name or number of the patient concerned.

As shown in FIG. 7, for example, a second embodiment of the urine sampler according to this invention is constituted as a urine collection device 10 consisting of a urine collector 11 and a urine storage capsule 15 that can be joined and separated. The urine collector 11 has a handle 12 and a urine collection member 13 formed integrally therewith, while the urine storage capsule 15 consists of a urine container 16, a cutter 17 and an integral lid 18.

In this embodiment, the urine collection member 13 and the urine accumulator 14 are formed integrally of the same material and the handle 12 is constituted as a long, hollow rod closed at the ends. Since the handle 12 is provided merely as a means for holding the urine collection member 13 and the urine accumulator 14, however, it does not necessarily have to be hollow and is not particularly limited as to material.

The urine collection member 13 is formed to extend integrally from the bottom end of the handle 12 in the shape of a cone. The outer surface of the cone is provided with urine collection apertures 131 which can be formed either by making cuts in the wall of the urine collection member 13 or by making holes therein.

Since the urine collection member flares conically, the subject is able to collect a urine sample in the urine collector simply and reliably, merely by urinating on the urine collecting member 13.

The urine accumulator 14 is a cylinder of the same diameter as the base of the conical urine collection member 13 and is formed integrally with urine collection member 13 to extend downward therefrom. As shown in FIG. 8, its bottom 141 is formed as a thin membrane that can be easily pierced by a sharp member (cutter). The bottom 141 can be formed of any material that can be easily pierced by a pointed object, typical examples being thin film of plastic and metal foil.

As shown in the sectional view of FIG. 9, the urine container 16 of the urine capsule 15 is a cylinder that is closed at the bottom and has an opening 165 at the top. It is larger in diameter than the urine accumulator 14 so that the bottom of the urine accumulator 14 can be fitted into the top of the urine capsule 15. As shown in the sectional view of FIG. 11, urine container 16 consists of an outer cylinder 161 constituting its outer wall and an inner cylinder 162 for holding urine disposed inside and concentrically with the outer cylinder 161. The space between the outer and inner cylinders is left empty.

A cutter 17 for piercing the bottom of the urine accumulator 14 is provided near the top of the inner cylinder 162. The cutter 17 has sharp projections constituting upward pointing blades 171. The present embodiment is provided with four blades 171 spaced regularly along the upper edge of the inner cylinder 162.

As shown in FIGS. 10 and 11, the lid 18 has a hinge member 181 by which it is integrally connected with the periphery of the outer cylinder 161 of the urine container 16. The lid 18 is formed to fit into the opening 65 of the urine container 16 snugly enough to prevent the urine contained in the urine container 16 from leaking out even if the urine storage capsule 15 should tip over. While in the present embodiment the snug fit is achieved by a one-touch operation, it is alternatively possible to use a screw-on type lid.

The method in which the stick type urine sampler is used for collecting a urine sample will now be explained along with a method for storing the sticks. The cap 6 is fitted onto the portion of the main stick body 1 above the corrugated section 3 prior to collecting a urine sample. The subject holds the top end of the stick so that the bottom end thereof (the plug 1a end) points sightly downward. Then, after starting to urinate, the subject moves the urine collection section 2a into and out of the urine stream so as to collect only the intermediate portion of the urine passed and not the first and last portions. Urine passed onto the urine collection section 2a flows through the holes formed by the cuts 2 into the interior of the stick and accumulates in the urine storage section 2b. At most, the urine accumulates to the level 40 in FIG. 3, at which an equilibrium is reached between the urine pressure and surface tension. However, when the urine adhering to the surface of the stick is wiped off using the cover cylinder 4 or the like, the urine level falls to 41. In effect, therefore, the amount of urine collected can be considered to be equal to the internal volume of the urine storage section 2b. If the amount of urine required for urinalysis differs depending on the purpose of the test, it suffices to change the length of the urine storage section accordingly.

Since the urine sampler according to this embodiment makes it possible to collect a urine sample merely by bringing the urine collection apertures into the urine stream, it can be easily used by anyone. Moreover, since the distance between the urine collection section 2a and the part of the main stick body 1 that is held with the hand (or in other embodiments, the handle 12) is greater than the splash-back distance of the urine striking the urine storage section 2a (urine collection member 13), any urine which splashes during sampling does not reach the hand holding the urine sampler. The sampling can thus be conducted in a sanitary manner.

After the urine sample has been taken, the cover cylinder 14, which is initially raised to the bottom edge of the corrugated section 3, is taken between the fingers and lowered to the upper end of the urine collection section 2a so as to wipe off any urine adhering to the surface of the stick. This ensures that urine will not get onto the hands or clothing of the user. Since the cover cylinder 14 has the inner cylinder portion 4b made of highly absorbent waste paper 4b, the urine adhering to the surface of the stick can be thoroughly removed. Although the surface tension inside the stick keeps the urine from flowing out of the urine storage section 2b even when the stick is held horizontally, the urine will flow out if the stick is laid on top of a desk or the like. To prevent this, the cap 6 is pulled off of the top end of the stick and pushed onto the bottom end of the stick until its upper end reaches the upper end of the urine collection section 2a. The urine sampler is then bent at the corrugated section near its upper end and stored, as shown in FIG. 4 for example, by hanging it from a wire 7a of a urine sampling stick holder 7 provided in the lavatory. When a number of samples are ready for testing, the urine sampling stick holder 7 is taken to the laboratory. Because of their small size, the urine sampling sticks take up less space in the laboratory than the same number of paper cups. Moreover, owing to the cap 6 fitted on the lower end of the stick and the effect of the internal surface tension, the collected urine does not leak from the stick even if it is tilted or dropped.

The method of conducting the urinalysis will not be explained. The main stick body 1 is held with its top end up as shown in FIG. 5, and a urinalysis test paper 8 with several urinalysis reagent patches is inserted from the upper end opening until it reaches the bottom end of the main stick body 1, so as to immerse the reagent section 8a in the urine. The urinalysis reagents thus react with the urine components. The test results are visually observed through the transparent main stick body 1 and recorded. Since there is no need to extract the test paper 8 from the stick, the tester's hands do not come in contact with the urine and the work can be can be conducted in a sanitary manner. Moreover, since only the minimum amount of urine required for testing is collected and this is held in the bottommost part of the stick covered by the cap 6, the tester is exposed to little if any unpleasant smell. After the results of the test have been recorded, the stick is discarded.

FIG. 6 shows another embodiment of the urine sampling stick in which the corrugated section 3 is formed in upper and lower segments, the cap 6 fitted snugly onto the main stick body 1 from the lower end thereof is made long enough to reach the lower segment of the corrugated section 3, and the cover 4 of the preceding embodiment is omitted. This arrangement also allows the stick to be handled without getting urine on the hands or clothes and enables the stick to be hung from the wire 7a of the urine sampling stick holder 7, after it has been bent at the upper segment of the corrugated section 3.

The method of collecting a urine sample using the urine collector shown in FIG. 8 and the method for transferring the collected sample to a urine storage capsule (the urine collector and the urine storage capsule together constituting another embodiment of this invention) will now be explained. When this embodiment is used for sampling urine, the patient grasps the upper part of the handle 12 of the urine collector 11 (with the urine storage capsule 15 detached), holds the urine collector 11 with the urine collection member 13 and the urine accumulator 14 pointing generally downward, and urinates onto the urine collection member 13. The urine striking the urine collection member 13 passes through the cuts or holes 131 formed in the surface of the urine collection member 13 and passes to the interior to collect in the urine accumulator 14. Preferably, the patient should collect only the intermediate portion of the urine passed and not the first and last portions. Since the urine collection member flares to a larger diameter than that of the handle 12, urine sampling is easier than it would otherwise be. If the amount of urine required for urinalysis differs depending on the purpose of the test, it suffices to change the amount of urine that is collected accordingly.

When the collected urine is to be transferred to the urine storage capsule, the urine collector 11 containing the sampled urine is pressed onto the opening 165 of the urine storage capsule 15 from above. As a result, the sharp blades 171 provided at the top of the urine storage capsule 15 rupture the thin membrane constituting the bottom 141 of the urine accumulator 14, whereby the urine held in the urine accumulator 14 flows into the urine container 16. After all of the sampled urine has passed into the urine container 16, the urine collector 11 is removed from the urine storage capsule 15 and the opening of the urine container 16 is closed and sealed with the lid 18. Later, after the lid has been opened in preparation for urinalysis, the urine can be transferred to a test tube and tested or can be tested by inserting a test paper into the urine while it is still in the urine storage capsule.

The embodiments of the urine sampler described in the foregoing have various advantages:

1. Since a sample can be collected merely by urinating onto the urine collection section/member, anyone is able to use the urine sampler without getting urine on the hands or clothes.
2. Since the sampled urine can be accumulated in the urine storage section/capsule more easily that in can be in the conventional paper cups, the urine sampler is easy and safe to use and also enables the urine to be moved from the lavatory or the like to the laboratory in a highly sanitary manner.
3. The collected samples are easy to store and large numbers of samples can be easily kept in order during storage and testing.
4. Since the urine sampler holds the urine sample in a sealed state that does not allow the odor of the urine to escape, the urinalysis can be conducted in a pleasant working environment without discomfort to those conducting the test.

5. In the case of the urine sampler having the urine storage capsule, the capsule can stand upright on its own, and since it is sealed with a tight lid, there is no danger of the sample spilling or splashing even if the capsule should be knocked off the testing table.

What is claimed is:

1. A urine sampler comprising a hollow, cylindrical main stick body closed at least at one end and having a plurality of urine collection apertures formed in a wall thereof wherein the urine collection apertures are diagonal cuts in the wall of the main stick body and the tips of the apertures project outwardly from the wall.

2. A urine sampler according to claim 1, wherein a part of the wall of the main stick body between the urine collection apertures and the end opposite said at least one end is formed into a corrugated section.

3. A urine sampler according to claim 2, further provided with a highly water absorbent cover cylinder fitted onto the main stick body to be slidable in close contact with the outer surface of the wall thereof between the urine collection apertures and the corrugated section.

4. A urine sampler according to claim 1, further comprising a cap snugly fittable onto said at least one end for closing the urine collection apertures.

5. A urine sampler according to claim 4, wherein the cap can be forced onto the main stick body until the open end thereof reaches the corrugated section.

6. A urine sampler according to claim 1, wherein a test paper can be inserted into the interior of the main stick body.

7. A urine sampler comprising:

a urine collector having:
 a long rod-shaped handle;
 a conical urine collection member having a narrow end and a broad end attached at the narrow end to the handle wherein urine collection apertures are disposed along the urine collection member; and
 a urine accumulator attached to the collection member near the broad end;

a urine storage capsule with a top having:
 a cutter for cutting a portion of the urine collector disposed near the top of the capsule;
 a urine container with an opening near the cutter for receiving urine flowing in from the urine collector; and
 a lid capable of sealing the opening of the container;

wherein a portion of the collector is capable of fitting into the opening of the container.

8. A urine sampler according to claim 7, wherein the handle of the urine collector is a hollow rod having ends which rod is closed at the ends, and wherein the urine accumulator is a cylindrical body having a top and a bottom closed at the bottom by an easily pierced thin member.

9. A urine sampler according to claim 7, wherein the cutter of the urine storage capsule is constituted of sharp blades, the urine storage container is a cylindrical body closed at the bottom, and the lid is formed to fit snugly into the opening of the urine container for preventing leakage of urine therefrom.

10. A urine sampler according to claim 8 or 9, wherein the urine collection apertures are cuts or holes.

* * * * *